United States Patent
Ishinabe et al.

(10) Patent No.: US 10,531,984 B2
(45) Date of Patent: Jan. 14, 2020

(54) OPHTHALMOLOGIC MICROSCOPE SYSTEM

(71) Applicant: KABUSHIKI KAISHA TOPCON, Itabashi-ku, Tokyo (JP)

(72) Inventors: Ikuo Ishinabe, Saitama (JP); Michiko Nakanishi, Katsushika (JP); Satoshi Yamamoto, Saitama (JP)

(73) Assignee: KABUSHIKI KAISHA TOPCON, Itabashi-ku, Tokyo (JP)

( * ) Notice: Subject to any disclaimer, the term of this patent is extended or adjusted under 35 U.S.C. 154(b) by 208 days.

(21) Appl. No.: 15/736,805

(22) PCT Filed: Feb. 3, 2016

(86) PCT No.: PCT/JP2016/053287
§ 371 (c)(1),
(2) Date: Dec. 15, 2017

(87) PCT Pub. No.: WO2017/002383
PCT Pub. Date: Jan. 5, 2017

(65) Prior Publication Data
US 2018/0177629 A1  Jun. 28, 2018

(30) Foreign Application Priority Data
Jun. 30, 2015 (JP) ................. 2015-132089

(51) Int. Cl.
*A61B 3/13* (2006.01)
*A61F 9/008* (2006.01)
(Continued)

(52) U.S. Cl.
CPC .............. *A61F 9/008* (2013.01); *A61B 3/107* (2013.01); *A61B 3/0025* (2013.01); *A61B 3/102* (2013.01);
(Continued)

(58) Field of Classification Search
CPC ......... A61B 3/13; A61B 3/107; A61B 3/0025; A61B 3/102; A61B 3/117; A61B 3/18;
(Continued)

(56) References Cited

U.S. PATENT DOCUMENTS

| 8,049,873 | B2 | 11/2011 | Hauger et al. |
| 2011/0228218 | A1 | 9/2011 | Hauger et al. |

(Continued)

FOREIGN PATENT DOCUMENTS

| JP | 2012-509729 A | 4/2012 |
| JP | 2015-058152 A | 3/2015 |
| WO | 2015/080137 A1 | 6/2015 |

OTHER PUBLICATIONS

International Search Report dated Apr. 19, 2016, in connection with International Patent Application No. PCT/JP2016/053287, 2 pgs.

*Primary Examiner* — Michael W Kahelin
(74) *Attorney, Agent, or Firm* — Chiesa Shahinian & Giantomasi PC

(57) ABSTRACT

An illumination system for projecting illumination light onto an eye. A left (right) light receiving system includes a left (right) objective lens and left (right) image sensor, and guides returning light of the illumination light to the left (right) image sensor via the left (right) objective lens. The objective optical axes of the left and right light receiving systems are disposed nonparallelly to each other. A projection system includes a projection system objective lens, and projects light onto the eye via the projection system objective lens. An optical scanner is used for scanning the eye with the light from the projection system. A deflection member is disposed near the objective optical axes, disposed in the optical path of the projection system between the optical scanner and the projection system objective lens, and deflects the optical path.

20 Claims, 9 Drawing Sheets

(51) Int. Cl.
 *A61B 3/107* (2006.01)
 *A61B 3/00* (2006.01)
 *A61B 3/10* (2006.01)
 *G02B 27/14* (2006.01)

(52) U.S. Cl.
 CPC ....... *A61B 3/13* (2013.01); *A61F 2009/00897* (2013.01); *G02B 27/14* (2013.01)

(58) Field of Classification Search
 CPC ....... A61B 3/0008; A61B 3/132; A61F 9/008; A61F 2009/00897; G02B 27/14; G02B 21/0004
 See application file for complete search history.

(56) References Cited

U.S. PATENT DOCUMENTS

| | | |
|---|---|---|
| 2015/0077707 A1 | 3/2015 | Hauger et al. |
| 2015/0077708 A1 | 3/2015 | Hauger et al. |
| 2017/0188819 A1 | 7/2017 | Hauger et al. |
| 2017/0188820 A1 | 7/2017 | Hauger et al. |

OPHTHALMOLOGIC MICROSCOPE SYSTEM

CROSS-REFERENCE TO RELATED APPLICATIONS

This application is a national stage (under 35 U.S.C. 371) of International Patent Application No. PCT/JP2016/053287, filed Feb. 3, 2016, claiming priority to Japanese Patent Application No. 2015-132089, filed Jun. 30, 2015, both of which are herein incorporated by reference in their entirety.

FIELD

Embodiments described herein relate generally to an ophthalmologic microscope system.

BACKGROUND

Various kinds of microscopes are utilized for magnifying observation of an eye in the field of ophthalmology. Examples of such ophthalmologic microscopes include slit lamp microscopes and surgical microscopes. There are ophthalmologic microscopes that include an image sensor for imaging an eye, and those that include a binocular optical system that provides binocular disparity for stereoscopic observation.

The ophthalmologic microscopes may be used in combination with another ophthalmologic apparatus. For example, a system is known in which an optical coherence tomography (OCT, hereinafter) apparatus or a laser treatment apparatus is combined with an ophthalmologic microscope. The OCT apparatus is utilized for, for example, acquiring cross sectional images of an eye, acquiring three dimensional images of an eye, measuring the sizes of ocular tissues (e.g., the thickness of the retina), and acquiring functional information on an eye (e.g., the blood flow information). The laser treatment apparatus is utilized for, for example, laser photocoagulation treatment of the retina, the corner angle, etc.

[Patent Document 1] U.S. Pat. No. 8,049,873.

The conventional ophthalmologic microscope system includes a Galilean stereo microscope. The Galilean stereo microscope is characterized in that the binocular optical system has a common objective lens and that the left and right optical axes of the binocular optical system are parallel to each other. The Galilean stereo microscope has an advantage of being able to combine other optical systems and optical elements easily. On the other hand, since it is necessary to use an objective lens with a large diameter, the Galilean stereo microscope has a disadvantage that the degree of flexibility in optical design or mechanism design is limited.

When another ophthalmologic apparatus such as an OCT apparatus is used in combination with an ophthalmologic microscope, it is necessary to arrange the optical path of the light projected by the OCT apparatus while making a way around the optical path of the binocular optical system, thereby making it difficult to project the light from the OCT apparatus onto the eye from the direction perpendicular to the eye. When the light from the OCT apparatus enters the eye from an oblique direction, the iris may cause the vignetting of the light or its returning light, and this may lead to a problem that the performance of the OCT apparatus cannot be sufficiently exerted.

SUMMARY

The present embodiment provides a novel configuration for solving the aforementioned problems related to the conventional ophthalmologic microscope system.

An ophthalmologic microscope system of an embodiment includes an illumination system, a left light receiving system, a right light receiving system, a projection system, an optical scanner, a deflection member. The illumination system is configured to project illumination light onto a subject's eye. The left light receiving system includes a left objective lens and a left image sensor, and is configured to guide returning light of the illumination light that has been projected onto the subject's eye to the left image sensor via the left objective lens. The right light receiving system includes a right objective lens and a right image sensor, and is configured to guide returning light of the illumination light that has been projected onto the subject's eye to the right image sensor via the right objective lens. In addition, an objective optical axis of the right light receiving system is disposed nonparallelly with respect to an objective optical axis of the left light receiving system. The projection system includes a projection system objective lens, and is configured to project light different from the illumination light onto the subject's eye via the projection system objective lens. The optical scanner is configured for scanning the subject's eye with the light from the projection system. The deflection member is disposed in the vicinity of a pair of objective optical axes which are respective optical axes of the left light receiving system and the right light receiving system, is disposed in an optical path of the projection system between the optical scanner and the projection system objective lens, and is configured to deflect the optical path.

DETAILED DESCRIPTION

Exemplary embodiments of an ophthalmologic microscope system according to the present invention will be described in detail with reference to the drawings. The contents of the documents cited in the present specification and any known techniques can be incorporated into the following embodiments.

An ophthalmologic microscope system is used for observing (and photographing) a magnified image of the subject's eye for a diagnosis, treatment and/or surgery in the field of ophthalmology. The site to be observed may be an arbitrary site of the patient's eye. For example, the site to be observed may be any site in the anterior eye segment such as the cornea, the corner angle, the vitreous body, the crystalline lens, or the ciliary body. In addition, the site to be observed may be any site in the posterior eye segment such as the retina, the choroid, or the vitreous body. The site to be observed may also be any peripheral site of the eye such as the eyelid or the eye socket.

In addition to the function as a microscope used for magnifying observation of the subject's eye, the ophthalmologic microscope system also has a function as another ophthalmologic apparatus. Examples of the function as another ophthalmologic apparatus include OCT, laser treatment, ocular axial length measurement, refractive power measurement, higher order aberration measurement, and the like. Another ophthalmologic apparatus has an arbitrary configuration capable of performing examination, measurement, and/or imaging of the subject's eye by means of an optical method. In the following embodiments, a configuration will be described in which an OCT function and a laser treatment function are combined with a microscope.

[Configuration]

Figure 1:
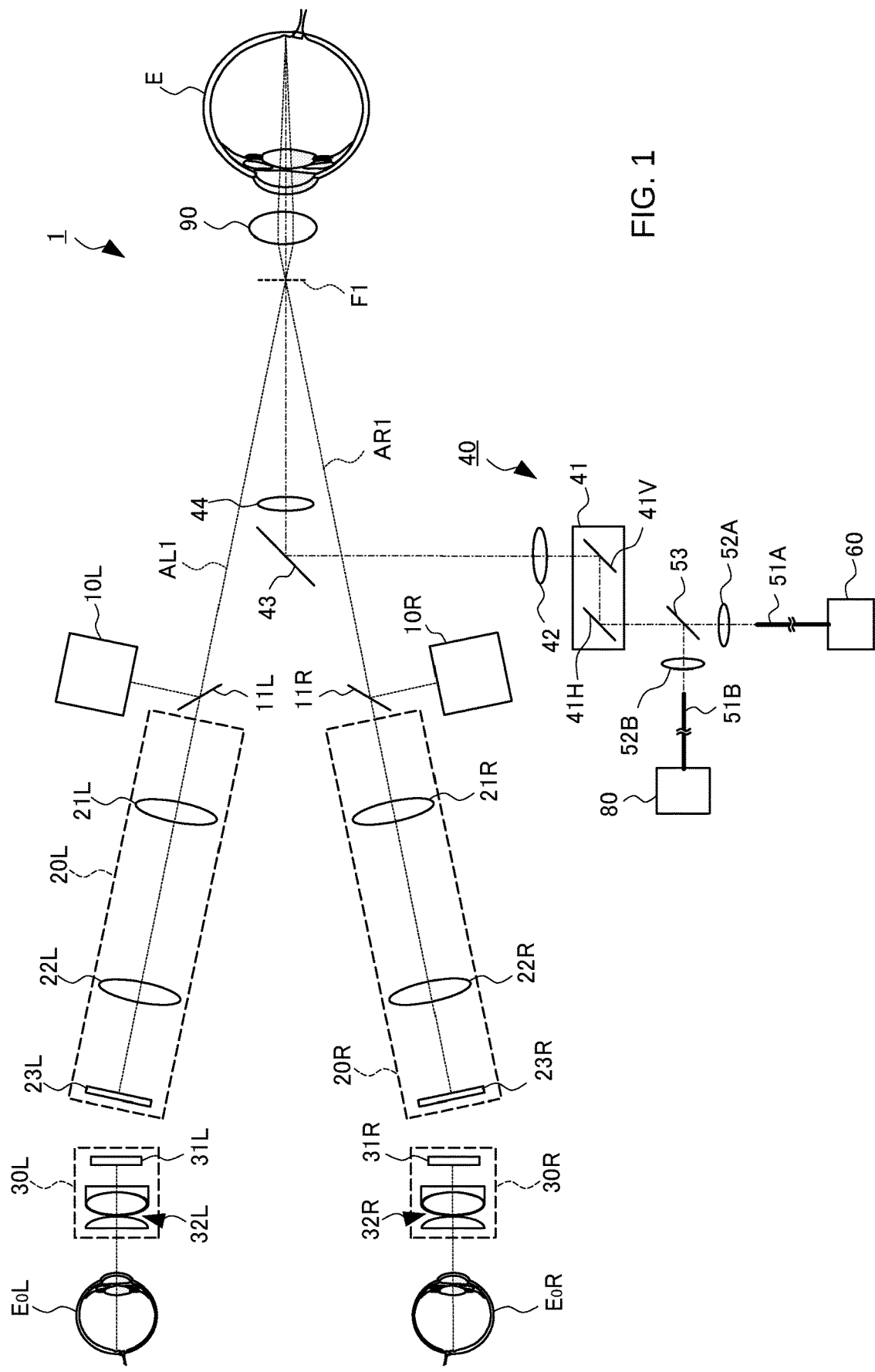
FIG. 1 is a schematic diagram illustrating an example of the configuration of the ophthalmologic microscope system according to the embodiment.
Figure 2:
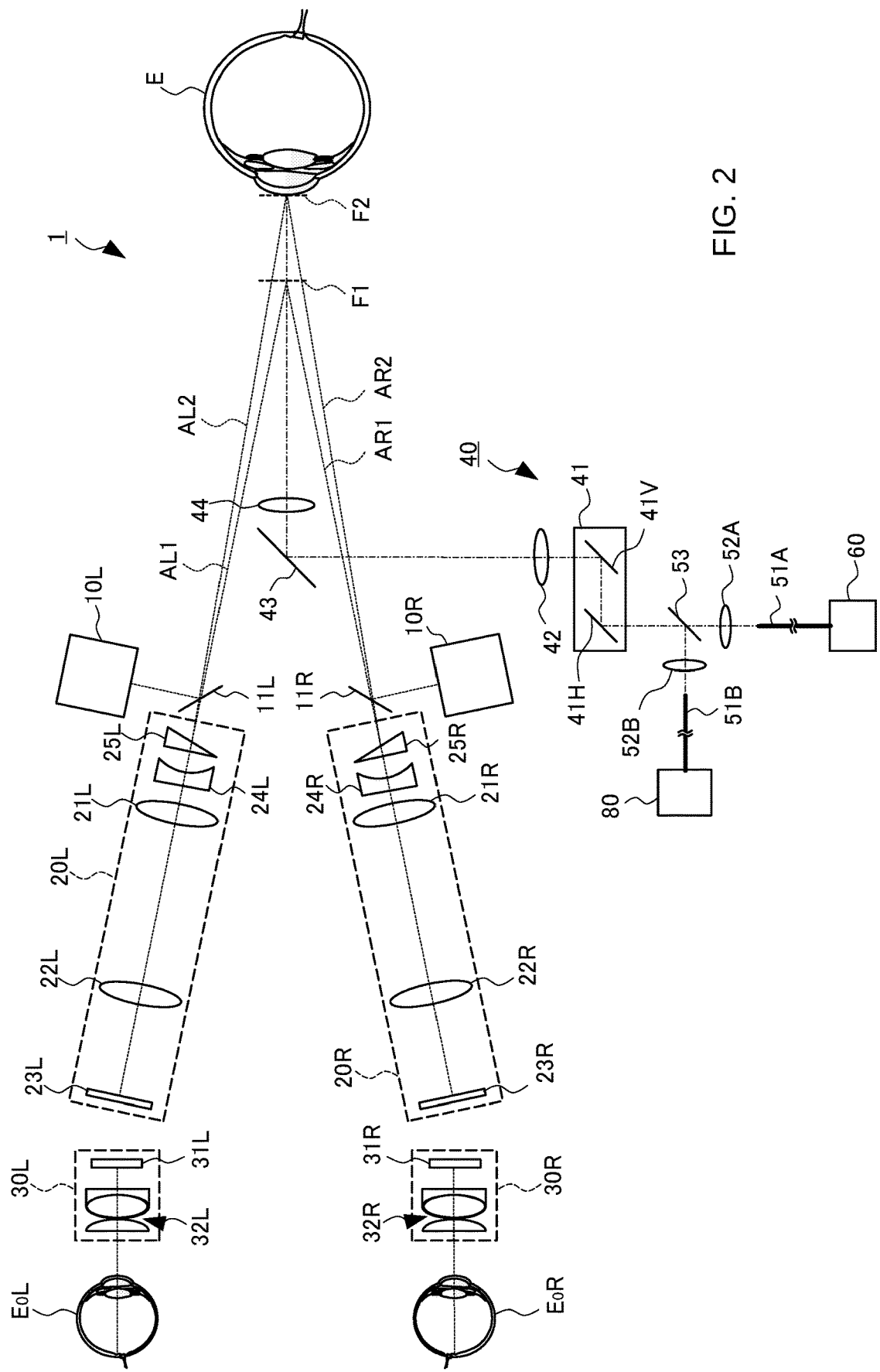
FIG. 2 is a schematic diagram illustrating an example of the configuration of the ophthalmologic microscope system according to the embodiment.
Figure 3:
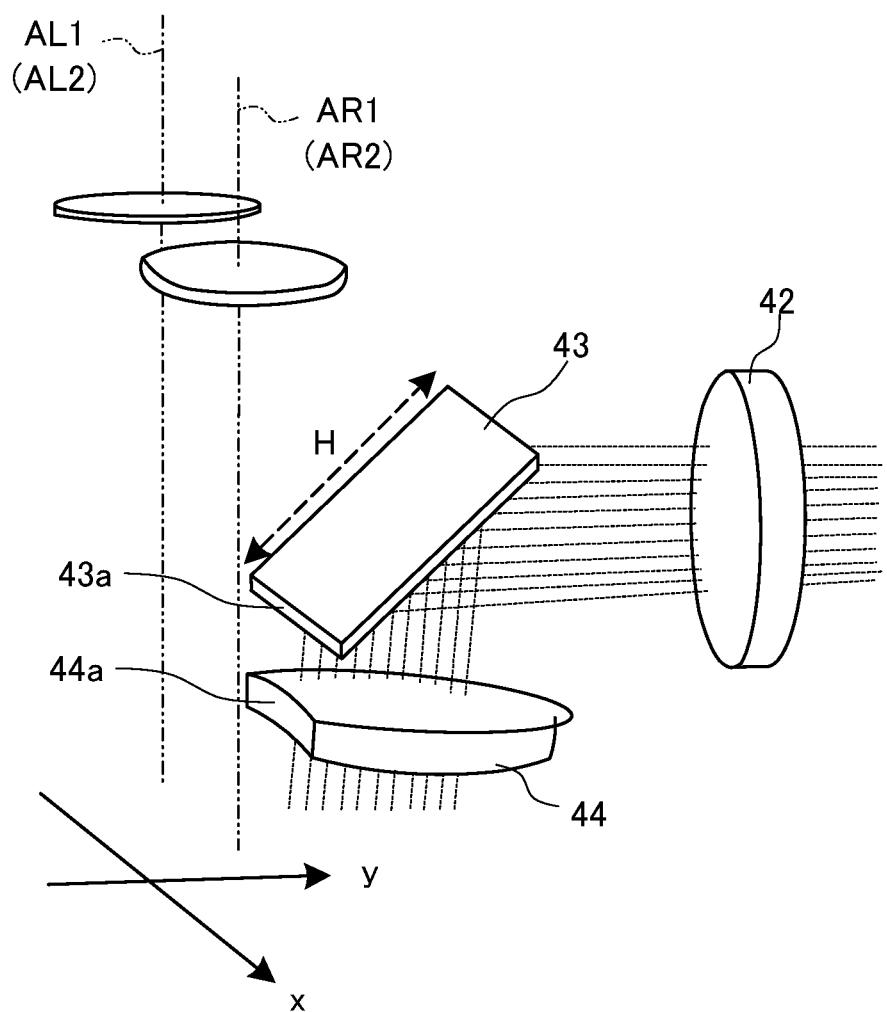
FIG. 3 is a schematic diagram illustrating an example of the configuration of the ophthalmologic microscope system according to the embodiment.
Figure 4:
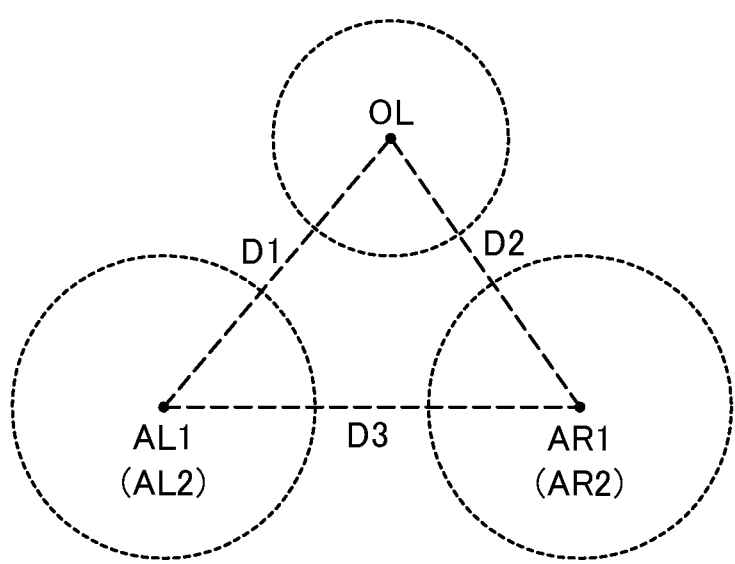
FIG. 4 is a schematic diagram illustrating an example of the configuration of the ophthalmologic microscope system according to the embodiment.
Figure 5:
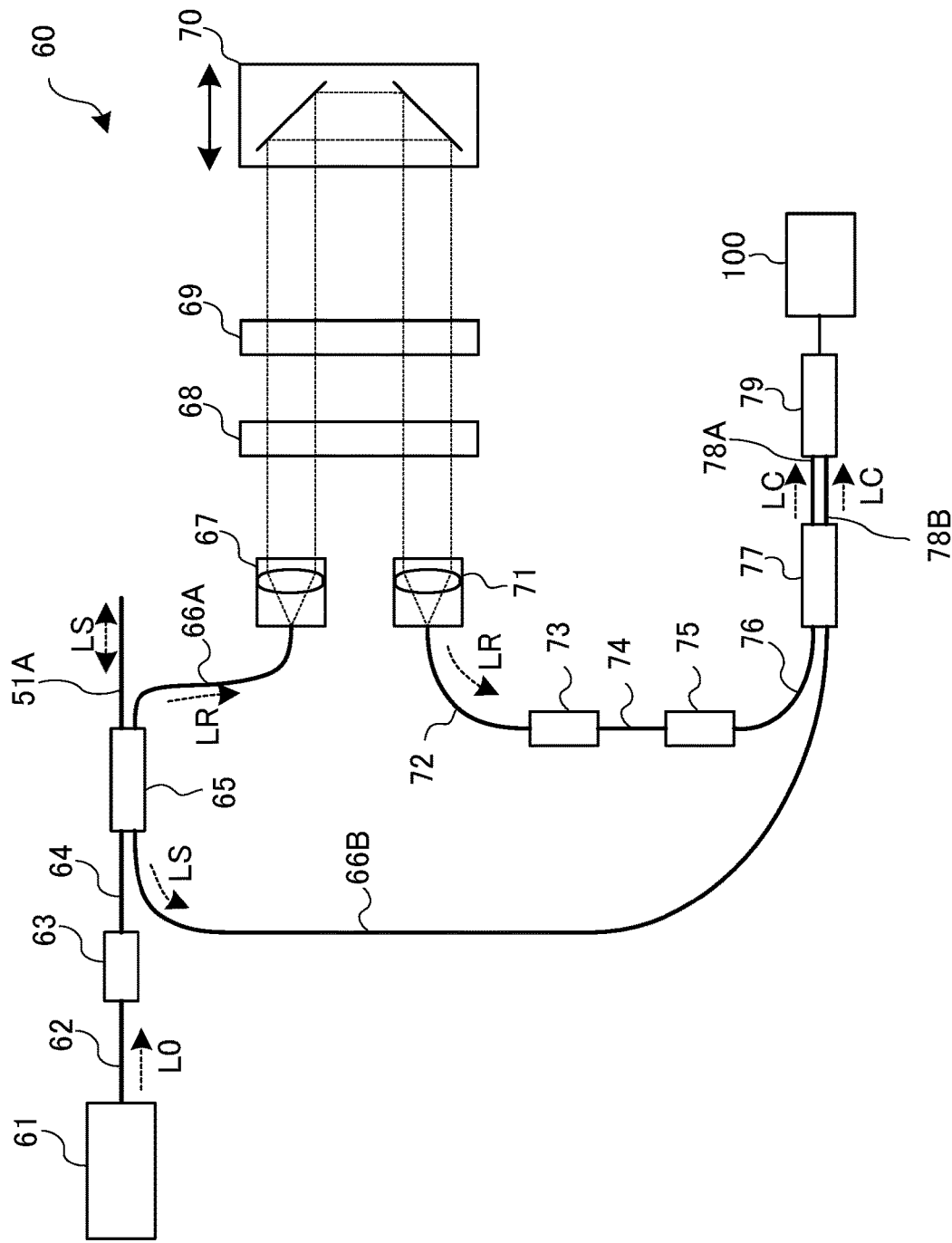
FIG. 5 is a schematic diagram illustrating an example of the configuration of the ophthalmologic microscope system according to the embodiment.
Figure 6:
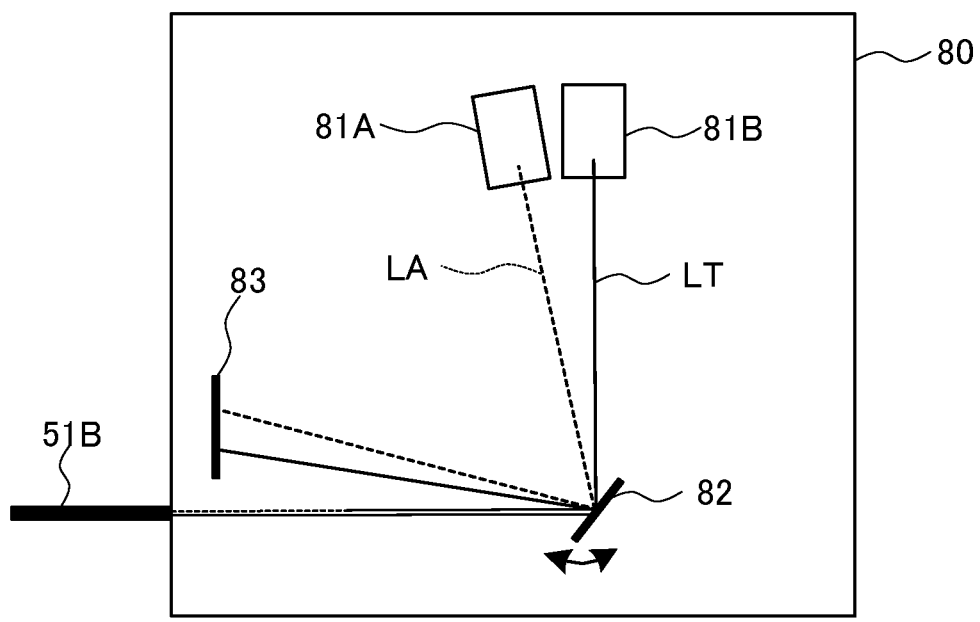
FIG. 6 is a schematic diagram illustrating an example of the configuration of the ophthalmologic microscope system according to the embodiment.
Figure 7:
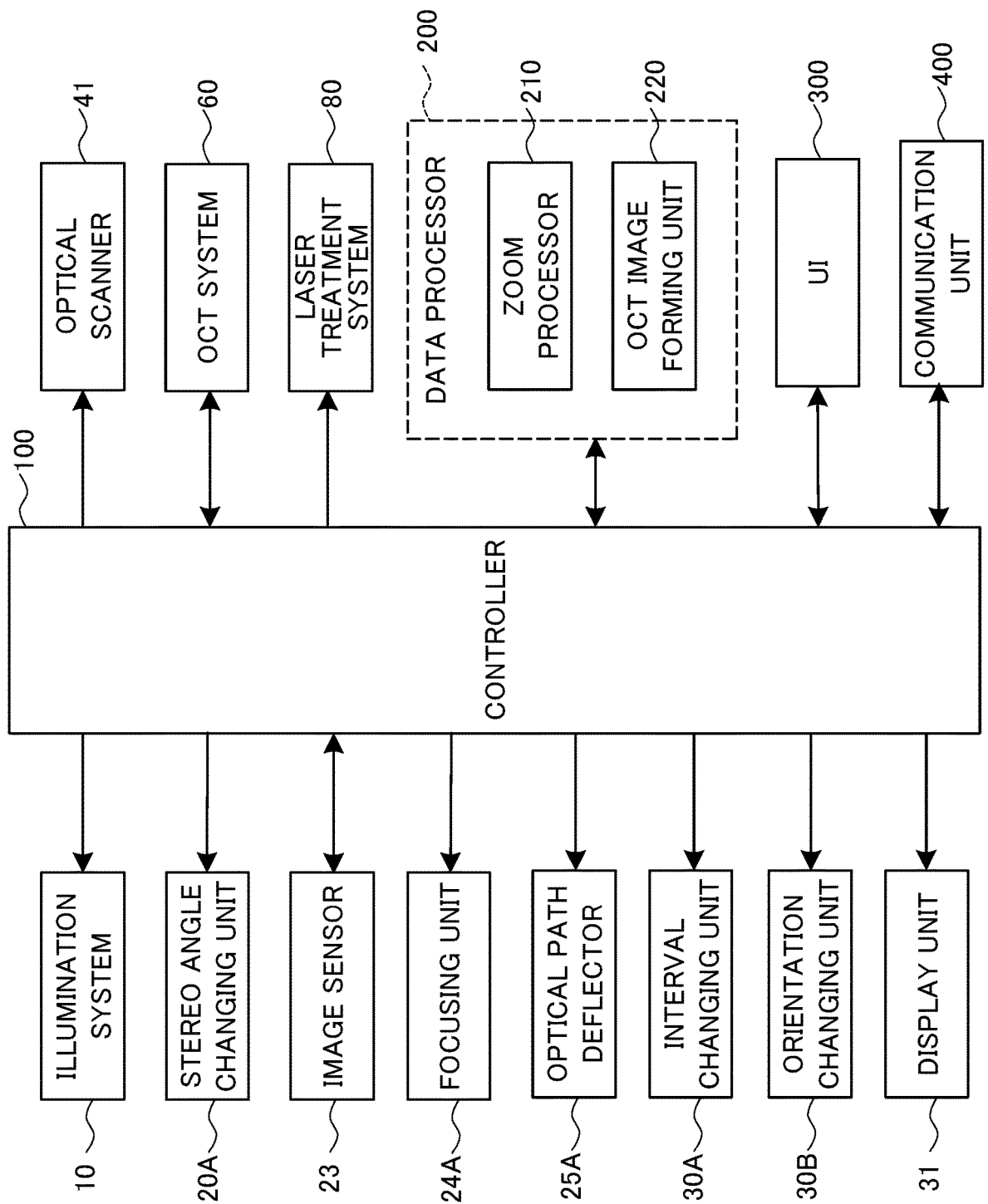
FIG. 7 is a schematic diagram illustrating an example of the configuration of the ophthalmologic microscope system according to the embodiment.

FIG. 1 to FIG. 8 illustrate an exemplary configuration of the ophthalmologic microscope system according to the embodiment. FIG. 1 to FIG. 4, and FIG. 8 illustrate an exemplary configuration of the optical system of the ophthalmologic microscope system. FIG. 1 illustrates the optical system used when observing the posterior eye segment, and FIG. 2 illustrates the optical system used when observing the anterior eye segment. FIG. 3 and FIG. 4 illustrate explanatory diagrams of the deflection mirror and the objective lens according to the embodiment. FIG. 5 and FIG. 6 illustrate an optical system for providing the "function as another ophthalmologic apparatus" mentioned above. FIG. 7 illustrates the configuration of the processing system.

The ophthalmologic microscope system 1 includes the illumination system 10 (10L and 10R), the light receiving system 20 (20L and 20 R), the eyepiece system 30 (30L and 30R), the projection system 40, the OCT system 60, and the laser treatment system 80. When observing the posterior eye segment (the retina, etc.), the front lens 90 is disposed right in front of the subject's eye E. Note that, a contact lens or the like can be used instead of the front lens 90 of a non-contact type as shown in FIG. 1. Also, a contact mirror (a triple mirror, etc.) or the like can be used when observing the corner angle.

(Illumination System 10)

The illumination system 10 projects illumination light onto the subject's eye E. Although not illustrated, the illumination system 10 includes a light source that emits illumination light, a diaphragm that defines an illumination field, a lens system, and the like. The illumination system may be configured in a similar manner to those of conventional ophthalmologic apparatuses (e.g., slit lamp microscopes, fundus cameras, refractometers, etc.).

The illumination systems 10L and 10R of the present embodiment are configured coaxially with the light receiving systems 20L and 20R, respectively. More specifically, the beam splitter 11L, which may be a half mirror, is obliquely positioned in the left light receiving system 20L that is used for acquiring an image to be presented to the left eye $E_OL$ of the observer. The beam splitter 11L couples the optical path of the left illumination system 10L to the optical path of the left light receiving system 20L in a coaxial fashion. The illumination light outputted from the left illumination system 10L is reflected by the beam splitter 11L and illuminates the subject's eye E coaxially with the left light receiving system 20L. Similarly, the beam splitter 11R, which couples the optical path of the right illumination system 10R to the optical path of the right light receiving system 20R, is obliquely positioned in the right light receiving system 20R that is used for acquiring an image to be presented to the right eye $E_OR$ of the observer. The beam splitter 11R couples the optical path of the right illumination system 10R to the optical path of the right light receiving system 20R in a coaxial fashion. The illumination light outputted from the right illumination system 10R is reflected by the beam splitter 11R and illuminates the subject's eye E coaxially with the right light receiving system 20R.

The position of the illumination light with respect to the optical axis of the light receiving system 20L (20R) can be changed. Such a configuration can be realized, for example, by providing a means for changing the projection position of the illumination light onto the beam splitter 11L (11R) like conventional microscopes for ophthalmologic surgery.

In the present example, the beam splitter 11L (11R) is disposed between the objective lens 21L (21R) and the subject's eye E; however, the position where the optical path of the illumination light is coupled to the light receiving system 20L (20R) may be an arbitrary position in the light receiving system 20L (20R).

(Light Receiving System 20)

The present embodiment includes a pair of left and right light receiving systems 20L and 20R. The left light receiving system 20L has a configuration for acquiring an image to be presented to the left eye $E_OL$ of the observer, and the right light receiving system 20R has a configuration for acquiring an image to be presented on the right eye $E_OR$. The left light receiving system 20L and the right light receiving system 20R have the same configuration. The left light receiving system 20L (the right light receiving system 20R) includes the objective lens 21L (21R), the imaging lens 22L (22R), and the image sensor 23L (23R).

A configuration in which the imaging lens 22L (22R) is not provided may also be employed. In the case where the imaging lens 22L (22R) is provided like the present embodiment, the optical path between the objective lens 21L (21R) and the imaging lens 22L (22R) can be configured to be an a focal optical path (a parallel optical path). This makes it easy to dispose an optical element such as a filter, and to dispose an optical path coupling member to couple an optical path from another optical system (in other words, the degree of flexibility and expandability of the configuration of the optical system are improved).

The reference symbol AL1 indicates the optical axis of the objective lens 21L (the objective optical axis) of the left light receiving system 20L, and the reference symbol AR1 indicates the optical axis of the objective lens 21R (the objective optical axis) of the right light receiving system 20R. The image sensor 23L (23R) is, for example, an area sensor such as a CCD image sensor or a CMOS image sensor.

The above is the configuration of the light receiving system 20 when observing the posterior segment (the fundus) of the subject's eye E (see FIG. 1). On the other hand, when observing the anterior eye segment, as shown in FIG. 2, the focus lens 24L (24R) and the wedge prism 25L (25R)

are disposed at positions on the subject's eye E side with respect to the objective lens 21L (21R). The focus lens 24L (24R) of the present example is a concave lens and acts to extend the focal length of the objective lens 21L (21R). The wedge prism 25L (25R) changes the direction of the optical path (i.e., the objective optical axis AL1 (AR1)) of the left light receiving system 20L (the right light receiving system 20R) outward by a predetermined angle. The optical axes deflected in this way are indicated by the reference symbols AL2 and AR2. In this manner, the focus lens 24L and the wedge prism 25L are disposed in the left light receiving system 20L, and the focus lens 24R and the wedge prism 25R are disposed in the right light receiving system 20R. As a result, the focal position F1 for posterior eye segment observation is switched to the focal position F2 for anterior eye segment observation.

A convex lens can be used as the focus lens. In that case, the focus lens is disposed in the optical path at the time of posterior eye segment observation, and removed from the optical path at the time of anterior eye segment observation. Instead of switching the focal length by inserting and removing the focus lens, it is possible to employ a configuration capable of changing the focal length in a continuous or stepwise manner, for example, by providing a focus lens that is movable in the direction along the optical axis.

In the example shown in FIG. 2, the base direction of the wedge prism 25L (25R) is outward (that is, the wedge prism 25L (25R) is disposed in a base-out manner); however, it is possible to apply a wedge prism disposed in a base-in manner. In that case, the wedge prism is disposed in the optical path at the time of observing the posterior eye segment, and removed from the optical path at the time of observing the anterior eye segment. Instead of switching the direction of the optical path by inserting and removing the wedge prism, the provision of a prism, whose prism power (and prism orientation) is variable, gives a configuration making it possible to change the direction of the optical path in a continuous or stepwise manner.

(Eyepiece System 30)

The present embodiment includes a pair of left and right eyepiece systems 30L and 30R. The left eyepiece system 30L has a configuration for presenting the image of the subject's eye E acquired by the left light receiving system 20L to the left eye $E_OL$ of the observer, and the right eyepiece system 30R has a configuration for presenting the image of the subject's eye E acquired by the right light receiving system 20R to the right eye $E_OR$. The left eyepiece system 30L and the right eyepiece system 30R have the same configuration. The left eyepiece system 30L (the right eyepiece system 30R) includes the display unit 31L (31R) and the eyepiece lens system 32L (32R).

The display unit 31L (31R) is, for example, a flat panel display such as an LCD. The size of the display surface of the display unit 31L (31R) is, for example, diagonal length of 7 inches or less. The screen sizes of the display devices provided in the pair of the left and right eyepiece systems 30L and 30R are determined under constraints such as the observer's eye width (the pupillary distance, etc.), the size of the apparatus, the design of the apparatus (the dispositions of the optical systems and mechanisms, etc.) and the like. In other words, there is a trade-off relationship between such constraint conditions and the size of the apparent field of view. From such a viewpoint, it is considered that the maximum screen size of the display units 31L and 31R is about 7 inches. On the other hand, by devising the configurations of the eyepiece lens systems 32L and 32R, the dispositions of the mechanisms, or the like, the display units 31L and 31R that have a screen size exceeding 7 inches can be employed, or the display units 31L and 31R of a small size can be employed.

The interval between the left eyepiece system 30L and the right eyepiece system 30R can be changed. With this, it becomes possible to adjust the interval between the left eyepiece system 30L and the right eyepiece system 30R according to the eye width of the observer. Further, the relative orientation between the left eyepiece system 30L and the right eyepiece system 30R can also be varied. That is, the angle formed between the optical axis of the left eyepiece system 30L and the optical axis of the right eyepiece system 30R can be changed. As a result of this, it becomes possible to induce the convergence of the both eyes $E_OL$ and $E_OR$, thereby being capable of supporting a stereoscopic view by the observer.

(Projection System 40)

The projection system 40 projects light for realizing the function as the aforementioned "another ophthalmologic apparatus" onto the subject's eye E from a direction different from those along the objective optical axes (AL1 and AR1, and, AL2 and AR2) of the light receiving system 20. The projection system 40 of the present example projects light for OCT (referred to as measurement light) and light for laser treatment (referred to as aiming light and treatment laser light) onto the subject's eye E.

The projection system 40 includes the optical scanner 41, the imaging lens 42, the deflection mirror 43, and the projection system objective lens 44. The light coming from the OCT system 60 and the light coming from the laser treatment system 80 are guided to the optical scanner 41.

The light coming from the OCT system 60 (measurement light) is guided through the optical fiber 51A and exits from the end face of the optical fiber 51A. The collimator lens 52A is disposed at a position facing the end face of the optical fiber 51A. The measurement light, which has been made into a parallel light beam by the collimator lens 52A, is led to the optical path coupling member 53 that couples the optical path for OCT and the optical path for laser treatment. On the other hand, the light coming from the laser treatment system 80 (aiming light or treatment laser light) is guided through the optical fiber 51B and exits from the end face of the optical fiber 51B. The collimator lens 52B is disposed at a position facing the end face of the optical fiber 51B. The light, which has been made into a parallel light beam by the collimator lens 52B, is led to the optical path coupling member 53.

When the wavelength for OCT is different from the wavelength for laser treatment, a dichroic mirror can be used as the optical path coupling member 53. Typically, broadband light having a center wavelength of about 1050 nm can be used as the light for OCT, and laser light having a wavelength of about 635 nm can be used as the light for laser treatment (the aiming light may be arbitrary visible light). On the other hand, when the two wavelengths are substantially the same or close to each other, a half mirror can be used as the optical path coupling member 53. As another example, when the timing of performing OCT is different from the timing of performing laser treatment, an optical path switching member such as a quick return mirror can be used as the optical path coupling member 53. In the example shown in FIG. 1 etc., the measurement light coming from the OCT system 60 passes through the optical path coupling member 53 and is incident on the optical scanner 41 while the light coming from the laser treatment system 80 is reflected by the optical path coupling member 53 and is incident on the optical scanner 41.

The optical scanner 41 is a two dimensional optical scanner, and includes the x scanner 41H that deflects light in the horizontal direction (x direction) and the y scanner 41V that deflects light in the vertical direction (y direction). Each of the x scanner 41H and the y scanner 41V may be an optical scanner of an arbitrary type. For example, a galvano mirror can be employed for each of the x scanner 41H and the y scanner 41V. The optical scanner 41 is disposed, for example, at the exit pupil positions of the collimator lens 52A and the collimator lens 52B or in the vicinity of the exit pupil positions. In addition, the optical scanner 41 is disposed, for example, at the entrance pupil position of the imaging lens 42 or in the vicinity of the entrance pupil position.

In the case where the two dimensional optical scanner is configured by combining two one dimensional optical scanners as in the present example, the two one dimensional optical scanners are disposed apart from each other by a predetermined distance (for example, about 10 mm). With this, for example, any one of the one dimensional optical scanners can be disposed at the aforementioned exit pupil positions and/or at the aforementioned entrance pupil position.

The imaging lens 42 once converges a parallel light beam (measurement light, aiming light, treatment laser light) that has passed through the optical scanner 41. The light having passed through the imaging lens 42 is reflected by the deflection mirror 43 toward the projection system objective lens 44. The light having passed through the projection system objective lens 44 is projected onto the subject's eye E.

The position of the deflection mirror 43 is determined in advance in such a manner that the light guided by the projection system 40 is projected onto the subject's eye E from a direction different from those along the objective optical axes (AL1 and AR1, and, AL2 and AR2) of the light receiving system 20. In the present example, the deflection mirror 43 is disposed at a position between the left light receiving system 20L and the right light receiving system 20R whose objective optical axes are arranged nonparallelly to each other.

FIG. 3 schematically shows a perspective view of the deflection mirror 43 and the projection system objective lens 44. FIG. 3 schematically illustrates a cross section of the optical path of the left light receiving system 20L in the direction perpendicular to the objective optical axis AL1 (AL2) and a cross section of the optical path of the right light receiving system 20R in the direction perpendicular to the objective optical axis AR1 (AR2).

In order to allow the light guided by the projection system 40 to be incident on the subject's eye E from an incidence direction that is as close as possible to the direction perpendicular to the subject's eye E, the deflection mirror 43 and the projection system objective lens 44 are arranged in the vicinity of the objective optical axes (AL1 and AR1, and, AL2 and AR2) of the light receiving system 20. The edge portion 43a of the deflection mirror 43 near the objective optical axis of the light receiving system 20 and the edge portion 44a of the projection system objective lens 44 near the objective optical axis of the light receiving system 20 are substantially in contact with the optical path of the left light receiving system 20L and the optical path of the right light receiving system 20R.

The optical scanner 41 and the deflection surface of the deflection mirror 43 are disposed in substantially optically conjugate manner to each other. In particular, the deflection surface of the y scanner 41V and the deflection surface of the deflection mirror 43, which are used to deflect the light coming from the projection system 40 in a direction substantially parallel to the objective optical axis of the light receiving system 20, are disposed in substantially optically conjugate manner with each other. In the present embodiment, the deflection surface of the y scanner 41V and the deflection surface of the deflection mirror 43, which deflect the light coming from the projection system 40 within the plane orthogonal to the plane that includes the pair of the objective optical axes of the light receiving system 20, are disposed in substantially optically conjugate manner with each other. With this, the size H (see FIG. 3) of the deflection surface of the deflection mirror 43 provided obliquely to the directions of the objective optical axes of the light receiving system 20 can reduced. By reducing the size H of the deflection mirror 43, it becomes possible to arrange the deflection mirror 43 and the projection system objective lens 44 even closer to the objective optical axes of the light receiving system 20.

In the present embodiment, the edge portion 44a of the projection system objective lens 44 near the objective optical axes of the light receiving system 20 is cut out in a linear shape. With this, the observation optical path of the left light receiving system 20L and the observation optical path of the right light receiving system 20R are not interrupted by the peripheral edge portion of the projection system objective lens 44. By cutting out the edge portion of the projection system objective lens 44, it becomes possible to dispose the deflection mirror 43 and the projection system objective lens 44 even closer to the objective optical axes of the light receiving system 20. It should be noted that the edge portion 44a may not be cut out in a linear shape but may be cut out, for example, in a curved shape.

The deflection mirror 43 is a reflection mirror in which the edge portion 43a of the deflection surface (reflection surface) thereof near the objective optical axes of the light receiving system 20 is formed in a linear shape. The edge portion 43a of the deflection mirror 43 and the edge portion 44a of the projection system objective lens 44 are disposed so as to be substantially in contact with the optical path of the left light receiving system 20L and the optical path of the right light receiving system 20R. With this, it becomes possible to dispose the deflection mirror 43 and the projection system objective lens 44 at a position as close as possible to the objective optical axes of the light receiving system 20.

FIG. 4 schematically shows optical path arrangement when the optical paths of the light receiving system 20 and that of the projection system 40 are viewed in the direction along the objective optical axes of the light receiving system 20. The objective optical axis AL1 (AL2) of the left light receiving system 20L is provided in the vicinity of the lens center of the left objective lens 21L. The objective optical axis AR1 (AR2) of the right light receiving system 20R is provided in the vicinity of the lens center of the right objective lens 21R. The objective optical axis OL of the projection system 40 is provided in the vicinity of the lens center of the projection system objective lens 44. The distance D1 between the lens center of the left objective lens 21L and the lens center of the projection system objective lens 44 is substantially equal to the distance D2 between the lens center of the right objective lens 21R and the lens center of the projection system objective lens 44. With this, the light coming from the projection system 40 can be made incident in the direction along the optical axis as close as possible to the objective optical axes of the light receiving system 20.

The distance D3 between the lens center of the left objective lens 21L and the lens center of the right objective lens 21R (i.e., the length of the base side) may be longer than the distances D1 and D2 (the lengths of the oblique sides). With this, the light coming from the projection system 40 can be made incident in the direction along the optical axis even closer to the objective optical axes of the light receiving system 20.

In the manner described above, the deflection mirror 43 and the projection system objective lens 44 can be disposed close to the objective optical axes of the light receiving system 20. With this, the light guided by the projection system 40 can be made incident on the subject's eye E from the incidence direction that is as close as possible to the direction perpendicular to the subject's eye E.

(OCT System 60)

The OCT system 60 includes an interference optical system for performing OCT. FIG. 5 shows an example of the configuration of the OCT system 60. The optical system shown in FIG. 5 is an example of swept source OCT. The optical system splits light emitted from a wavelength scanning type (wavelength tunable type) light source into measurement light and reference light, generates interference light by superposing the returning light of the measurement light from the subject's eye E and the reference light that has traveled through the reference optical path, and detects the interference light. The detection result (detection signal) of the interference light obtained by the interference optical system is a signal indicating a spectrum of the interference light, and is sent to the controller 100.

Like general swept source OCT apparatuses, the light source unit 61 includes a wavelength scanning type (wavelength tunable type) light source that is capable of scanning (sweeping) the wavelength of emitted light. The light source unit 61 temporally changes the output wavelength within the near infrared wavelength band that cannot be visually recognized by human eyes.

The light L0 output from the light source unit 61 is guided to the polarization controller 63 by the optical fiber 62, and the polarization state of the light L0 is regulated. Then, the light L0 is guided to the fiber coupler 65 through the optical fiber 64. The fiber coupler 65 splits the light L0 into the measurement light LS and the reference light LR.

The reference light LR is guided to the collimator 67 by the optical fiber 66A. The reference light LR is converted into a parallel light beam by the collimator 67. Then, the reference light LR is guided to the corner cube 70 via the optical path length correction member 68 and the dispersion compensation member 69. The optical path length correction member 68 acts as a delaying element for matching the optical path length (optical distance) of the reference light LR and that of the measurement light LS. The dispersion compensation member 69 acts as a dispersion compensating element for matching the dispersion characteristic of the reference light LR and that of the measurement light LS.

The corner cube 70 changes the traveling direction of the reference light LR in the opposite direction. The corner cube 70 is movable in the direction along the incident optical path and the outputting optical path of the reference light LR. With this, the length of the optical path of the reference light LR is changed. It should be noted that it is sufficient to provide any one of a means for changing the length of the optical path of the measurement light LS and a means for changing the length of the optical path of the reference light LR.

The reference light LR that has passed through the corner cube 70 travels through the dispersion compensation member 69 and the optical path length correction member 68, is converted from the parallel light beam into a convergent light beam by the collimator 71, enters the optical fiber 72, and is guided to the polarization controller 73. The polarization controller 73 regulates the polarization state of the reference light LR. Subsequently, the reference light LR is guided to the attenuator 75 by the optical fiber 74, and the light amount is regulated under the control of the controller 100. The reference light LR whose light amount has been regulated is guided to the fiber coupler 77 by the optical fiber 76.

Meanwhile, the measurement light LS generated by the fiber coupler 65 is guided by the optical fiber 51A, is emitted from its fiber end face, and is made into a parallel light beam by the collimator lens 52A. The measurement light LS that has been made into the parallel light beam is projected onto the subject's eye E via the optical path coupling member 53, the optical scanner 41, the imaging lens 42, the deflection mirror 43, and the projection system objective lens 44. The measurement light LS is reflected and scattered at various depth positions of the subject's eye E. The returning light of the measurement light LS from the subject's eye E includes reflected light and backscattered light, advances along the same route as the forward path in the opposite direction, is led to the fiber coupler 65, and then reaches the fiber coupler 77 via the optical fiber 66B.

The fiber coupler 77 generates the interference light by superposing the measurement light LS incident via the optical fiber 66B and the reference light LR incident via the optical fiber 76 with each other (that is, by making the measurement light LS incident through the optical fiber 66B and the reference light LR incident through the optical fiber 76 interfere with each other). The fiber coupler 77 splits the interference light at a predetermined branching ratio (for example, 1:1) to generate a pair of the interference light beams LC. The pair of interference light beams LC emitted from the fiber coupler 77 are guided to the detector 79 by the optical fibers 78A and 78B, respectively.

The detector 79 is, for example, a balanced photo diode. The balanced photo diode includes a pair of photodetectors that respectively detect the pair of interference light beams LC, and outputs the difference between the detection results obtained by the pair of photodetectors. The detector 79 sends the detection result (detection signal) to the controller 100.

Although swept source OCT is employed in the present example, it is also possible to employ other types of OCT such as spectral domain OCT.

(Laser Treatment System 80)

The laser treatment system 80 includes a configuration for performing laser treatment. In particular, the laser treatment system 80 generates light to be projected on the subject's eye E. FIG. 6 shows an exemplary configuration of the laser treatment system 80. The laser treatment system 80 includes the aiming light source 81A, the treatment light source 81B, the galvano mirror 82, and the light shielding plate 83. In addition, members other than these can be provided in the laser treatment system 80. For example, an optical element (such as a lens) that makes the light generated by the laser treatment system 80 enter the end face of the optical fiber 51B can be provided at a position right in front of the optical fiber 51B.

The aiming light source 81A generates the aiming light LA for aiming at a site to be subjected to laser treatment. An arbitrary light source is used as the aiming light source 81A. In the present embodiment, a configuration is employed in which the aiming is performed while observing the photographed image of the subject's eye E. Therefore, a light source (such as a laser light source or a light emitting diode) that emits light in a wavelength band in which the imaging element 23 (23L and 23R) has sensitivity is used as the aiming light source 81A. When a configuration in which the aiming is performed by visual observation is employed, visible light is used as the aiming light LA. The aiming light LA is guided to the galvano mirror 82.

The treatment light source 81B emits treatment laser light (treatment light LT). The treatment light LT may be visible laser light or invisible laser light depending on its purpose of use. In addition, the treatment light source 81B may be a single laser light source or a plurality of laser light sources emitting laser light of different wavelengths. The treatment light LT is guided to the galvano mirror 82.

The aiming light LA and the treatment light LT reach the same position on the reflection surface of the galvano mirror 82. Note that the aiming light LA and the treatment light LT are sometimes collectively referred to as "projection light". The orientation of the galvano mirror 82 (the orientation of the reflection surface of the galvano mirror 82) is changed to at least an orientation for reflecting the projection light toward the optical fiber 51B (the orientation for projection) and an orientation for reflecting the projection light toward the light shielding plate 83 (the orientation for stopping).

When the galvano mirror 82 is arranged in the orientation for stopping, the projection light reaches the light shielding plate 83. The light shielding plate 83 is, for example, a member made of a material that absorbs the projection light and/or a member with a form that absorbs the projection light to exhibit light shielding function.

In the present embodiment, the aiming light source 81A and the treatment light source 81B each generate light continuously. By arranging the galvano mirror 82 in the orientation for projection, the projection light is projected onto the subject's eye E. Further, by arranging the galvano mirror 82 in the orientation for stopping, the projection of the projection light onto the subject's eye E is stopped. In other embodiments, the aiming light source 81A and/or the treatment light source 81B may be configured to intermittently generate light. That is, the aiming light source 81A and/or the treatment light source 81B may be configured to be capable of generating pulsed light. The pulse control for this purpose is executed by the controller 100. When this configuration is employed, it is not necessary to provide the galvano mirror 82 and the light shielding plate 83.

The image sensor 23L is an example of the "left image sensor" according to the embodiment. The image sensor 23R is an example of the "right image sensor" according to the embodiment. The deflection mirror 43 is an example of the "deflection member" according to the embodiment. The beam splitter 11L is an example of the "left optical path coupling member" according to the embodiment. The beam splitter 11R is an example of the "right optical path coupling member" according to the embodiment. The y scanner 41V is an example of the "one dimensional scanner" according to the embodiment. The OCT system 60 is an example of the "interference optical system" according to the embodiment.

(Controller 100)

The controller 100 executes control of each part of the ophthalmologic microscope system 1 (see FIG. 7). Examples of the control for the illumination system 10 include the followings: turning on of the light source, turning off of the light source, regulation of the light amount of the light source; regulation of the diaphragm; and regulation of the slit width in the case where illumination with slit light is possible. Examples of the control for the image sensor 23 include exposure regulation, gain regulation, and photographing rate regulation.

The controller 100 controls the display unit 31 to display various kinds of information. For example, the controller 100 controls the display unit 31L to display an image acquired by the image sensor 23L (or an image constructed by processing the image acquired by the image sensor 23L), and controls the display unit 31R to display an image acquired by the image sensor 23R (or an image constructed by processing the image acquired by the image sensor 23R).

As exemplary control for the optical scanner 41, the measurement light LS is deflected in a sequential manner such that the measurement light LS is projected to a plurality of locations according to an OCT scan pattern set in advance. Further, as another exemplary control for the optical scanner 41, the aiming light LA and/or the treatment light LT can be sequentially redirected in such a manner that the aiming light LA and/or the treatment light LT is projected to a plurality of locations according to a laser treatment pattern set in advance.

Parts of the OCT system 60 to be controlled include the light source unit 61, the polarization controller 63, the corner cube 70, the polarization controller 73, the attenuator 75, and the detector 79. Parts of the laser treatment system 80 to be controlled include the aiming light source 81A, the treatment light source 81B, and the galvano mirror 82.

In addition, the controller 100 controls various mechanisms. As such mechanisms, provided are the stereo angle changing unit 20A, the focusing unit 24A, the optical path deflector 25A, the interval changing unit 30A, and the orientation changing unit 30B.

The stereo angle changing unit 20A relatively rotates the left light receiving system 20L and the right light receiving system 20R. That is, the stereo angle changing unit 20A relatively moves the left light receiving system 20L and the right light receiving system 20R so as to change the angle formed by their objective optical axes (AL1 and AR1, for example). This relative movement is performed, for example, in such a manner that the left light receiving system 20L and the right light receiving system 20R are moved by the same angle in the opposite rotation direction. In this movement mode, the orientation of the bisector of the angle formed by the objective optical axes (AL1 and AR1, for example) is fixed. On the other hand, it is also possible to perform the aforementioned relative movement in such a manner that the orientation of the bisector changes.

Figure 8:
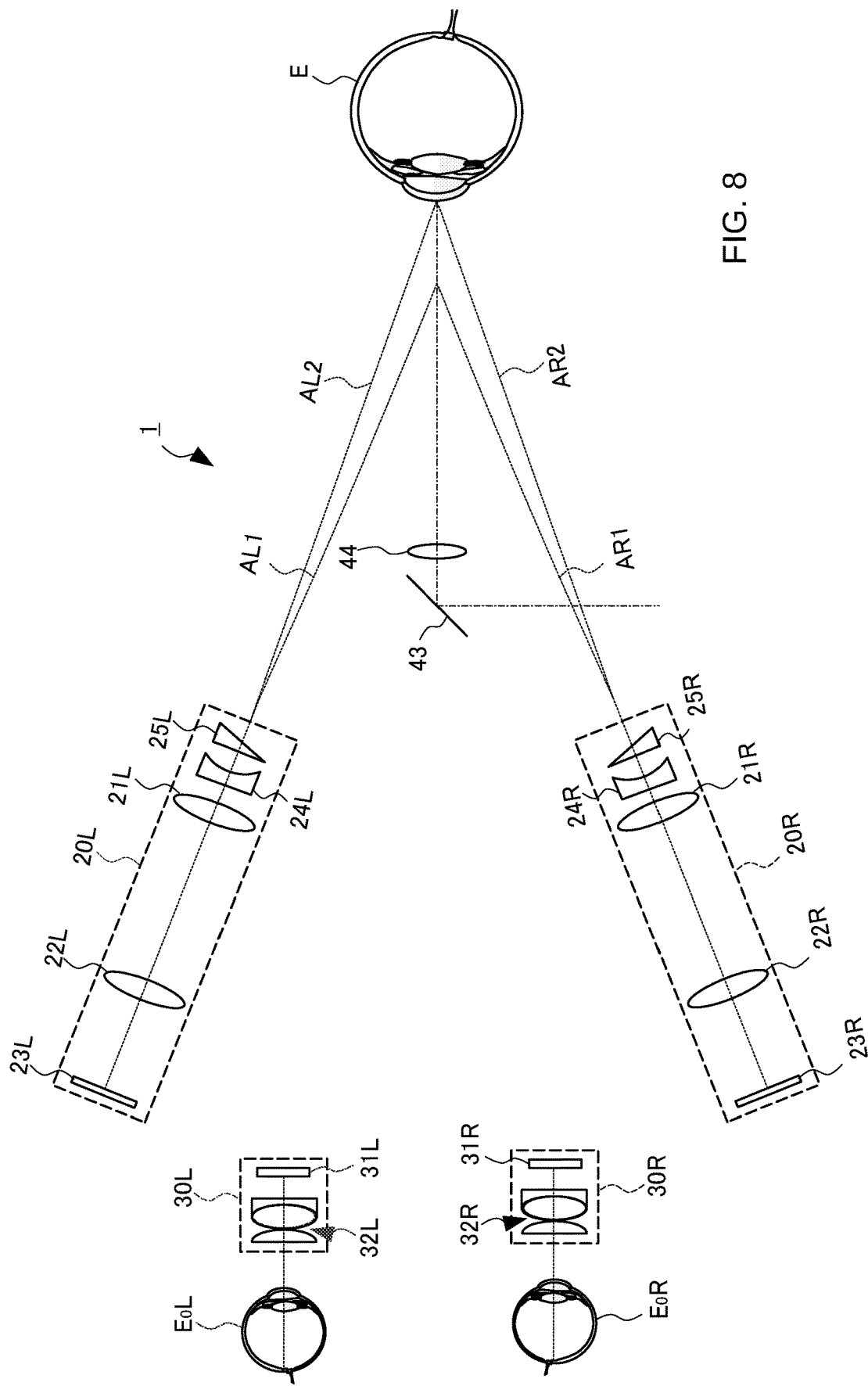
FIG. 8 is a schematic diagram illustrating an action of the ophthalmologic microscope system according to the embodiment.

FIG. 8 shows an example of a state in which the stereo angle has been increased from the state shown in FIG. 2. Note that the stereo angle may be defined as an angle formed by the objective optical axis AL1 of the left light receiving system 20L and the objective optical axis AR1 of the right light receiving system 20R, or may be defined as an angle formed by the objective optical axis AL2 of the left light receiving system 20L and the objective optical axis AR2 of the right light receiving system 20R. Even when the stereo angle is changed by the stereo angle changing unit 20A, the relative positions (interval, relative orientation) of the left and right eyepiece systems 30L and 30R do not change. Also, it is possible to execute control in such a manner that the focal position does not move by adjusting the distance between the left and right light receiving systems 20L and 20R with respect to the subject's eye E and/or by changing the focal lengths of the left and right light receiving systems 20L and 20R in response to the change in the stereo angle.

The focusing unit 24A inserts and removes the left and right focus lenses 24L and 24R into and from the respective optical paths. The focusing unit 24A may be configured to simultaneously insert and remove the left and right focus lenses 24L and 24R. In another example, the focusing unit 24A may be configured to change the focal position by moving the left and right focus lenses 24L and 24R (simultaneously) in the respective directions along the optical axes. Alternatively, the focusing unit 24A may be configured to change the focal lengths by (simultaneously) changing the refractive powers of the left and right focus lenses 24L and 24R.

The optical path deflector 25A inserts and removes the left and right wedge prisms 25L and 25R into and from the respective optical paths. The optical path deflector 25A may be configured to simultaneously insert and remove the left and right wedge prisms 25L and 25R. In another example, the optical path deflector 25A may be configured to (simultaneously) change the prism powers (and the prism orientations) of the left and right wedge prisms 25L and 25R to change the orientations of the optical paths of the left and right light receiving systems 20L and 20R.

The interval changing unit 30A changes the interval between the left and right eyepiece systems 30L and 30R. The interval changing unit 30A may be configured to relatively move the left and right eyepiece systems 30L and 30R without changing the relative orientation of their optical axes.

The orientation changing unit 30B changes the relative orientation of the left and right eyepiece systems 30L and 30R. The orientation changing unit 30B relatively moves the left eyepiece system 30L and the right eyepiece system 30R so as to change the angle formed by the respective optical axes. This relative movement is performed, for example, in such a manner that the left eyepiece system 30L and the right eyepiece system 30R are moved by the same angle in the opposite rotation direction. In this movement mode, the orientation of the bisector of the angle formed by the respective optical axes is fixed. On the other hand, it is also possible to perform the aforementioned relative movement in such a manner that the orientation of the bisector changes.

(Data Processor 200)

The data processor 200 executes various kinds of data processing. Examples of the data processing include a process of forming an image, and a process of manipulating (processing) an image. In addition, the data processor 200 may be capable of executing an analysis process of an image, an analysis process of an examination result, an analysis process of a measurement result, or a process relating to information on a subject (such as electronic medical record information). The data processor 200 includes the zoom processor 210 and the OCT image forming unit 220.

The zoom processor 210 enlarges an image acquired by the image sensor 23. This processing is so-called digital zoom processing, and includes a process of clipping a part of the image acquired by the image sensor 23 and a process of generating an enlarged image of the part clipped. An area of the image to be clipped is set by the observer or by the controller 100. The zoom processor 210 applies the same processing to an image (left image) acquired by the image sensor 23L of the left light receiving system 20L and to the image (right image) acquired by the image sensor 23R of the right light receiving system 20R. With this, images of the same magnification are presented to the left eye $E_OL$ and the right eye $E_OR$ of the observer.

Note that it is possible to provide a so-called optical zoom function in addition to or in place of the digital zoom function described above. The optical zoom function is realized by providing a zoom lens (a zoom lens system) in each of the left and right light receiving systems 20L and 20R. As a specific example, the optical zoom function is realized by employing a configuration in which the zoom lenses can be (selectively) inserted into and removed from the respective optical paths, or a configuration in which the zoom lenses can be moved in the directions along the respective optical axes. Control relating to the optical zoom function is executed by the controller 100.

The OCT image forming unit 220 forms an image of the subject's eye E based on detection results of the interference light LC acquired by the detector 79 of the OCT system 60. The controller 100 sends the detection signals sequentially output from the detector 79, to the OCT image forming unit 220. The OCT image forming unit 220 forms a reflection intensity profile for each A line by applying Fourier transform etc. to the spectral distribution on the basis of the detection results acquired by the detector 79 for each series of wavelength scans (i.e., for each A line), for example. In addition, the OCT image forming unit 220 forms image data by applying an imaging process to each A line profile. With this, a B scan image (cross sectional image), volume data (three dimensional image data), and the like are obtained.

The data processor 200 may have a function of analyzing an image (OCT image) formed by the OCT image forming unit 220. Examples of such an analysis function include retinal thickness analysis, and comparative analysis with normal eyes. The analysis function is executed using a known application. Further, the data processor 200 may have a function of analyzing an image acquired by the light receiving system 20. In addition, the data processor 200 may have an analysis function that is a combination of the analysis of an image acquired by the light receiving system 20 and the analysis of an OCT image.

(User Interface 300)

The user interface (UI) 300 has a function for exchanging information between the observer or the like and the ophthalmologic microscope system 1. The user interface 300 includes a display device and an operation device (an input device). The display device may include the display unit 31 and may include other display devices. The operation device includes various kinds of hardware keys and/or various kinds of software keys. It is possible to integrate at least part of the operation devices and at least part of the display devices. An example of such an integrated configuration is a touch panel display.

(Communication Unit 400)

The communication unit 400 performs a process of sending information to other apparatuses and a process of receiving information sent from other apparatuses. The communication unit 400 may include a communication device conforming to a predetermined network (such as a LAN and the Internet). For example, the communication unit 400 acquires information from an electronic medical record database or a medical image database via a LAN provided in a medical institution. In the case where an external monitor is provided, the communication unit 400 can send an image (such as an image acquired by the light receiving system 20, or an OCT image) acquired by the ophthalmologic microscope system 1 to the external monitor substantially in real time.

[Effects]

Effects of the ophthalmologic microscope system of the embodiment will be described.

The ophthalmologic microscope system according to the embodiment includes an illumination system (the illumination system 10), a left light receiving system (the left light receiving system 20L), a right light receiving system (the right light receiving system 20R), a projection system (the projection system 40), an optical scanner (the optical scanner 41), and a deflection member (the deflection mirror 43). The illumination system is configured to project illumination light onto a subject's eye (the subject's eye E). The left light receiving system includes a left objective lens (the left objective lens 21L) and a left image sensor (the left image sensor 23L), and is configured to guide the returning light of the illumination light that has been projected onto the subject's eye to the left image sensor via the left objective lens. The right light receiving system includes a right objective lens (the right objective lens 21R) and a right image sensor (the right image sensor 23R). The right light receiving system is configured to guide the returning light of the illumination light that has been projected onto the subject's eye to the right image sensor via the right objective lens. Here, the objective optical axis of the right light receiving system (the objective optical axis AR1 (AR2)) is disposed nonparallelly with respect to the objective optical axis of the left light receiving system (the objective optical axis AL1 (AL2)). The projection system includes a projection system objective lens (the projection system objective lens 44), and is configured to project light different from the illumination light onto the subject's eye via the projection system objective lens. The optical scanner is used for scanning the subject's eye with the light from the projection system. The deflection member is disposed in a vicinity of a pair of the objective optical axes which are respective optical axes of the left light receiving system and the right light receiving system. Further, the deflection member is disposed in the optical path of the projection system between the optical scanner and the projection system objective lens. In addition, the deflection member is configured to deflect the optical path of the projection system.

According to such a configuration, the deflection member and the projection system objective lens are disposed in the vicinity of the objective optical axes of the left light receiving system and the right light receiving system. Therefore, the light guided by the projection system can be made incident on the subject's eye from the incidence direction that is as close as possible to the direction perpendicular to the subject's eye. With this, it becomes possible to project a sufficient light amount of the light from the projection system onto the subject's eye and to detect a sufficient light amount of the returning light from the subject's eye with the absence of vignetting of the incident light and its returning light due to the iris of the subject's eye.

In the ophthalmologic microscope system according to the embodiment, the optical scanner may include a one dimensional scanner (the y scanner 41V). The one dimensional scanner is configured to deflect the light from the projection system in a direction substantially parallel to at least one of the objective axes of the left light receiving system and the right light receiving system. The one dimensional scanner and the deflection member are disposed at positions substantially optically conjugate with each other.

According to such a configuration, the size of the deflection member can be reduced. Therefore, it becomes possible to dispose the deflection member and the projection system objective lens even closer to the objective optical axes of the left light receiving system and the right light receiving system. As a result, the light from the projection system can be made incident on the subject's eye from an incidence direction that is even closer to the direction perpendicular to the subject's eye.

In the ophthalmologic microscope system according to the embodiment, an edge portion (the edge portion 44a) of the projection system objective lens near the pair of objective optical axes may be cut out.

According to such a configuration, it is possible to prevent the projection system objective lens from blocking the optical paths of the left light receiving system and the right light receiving system. This makes it possible to dispose the deflection member and the projection system objective lens even closer to the objective optical axes of the left light receiving system and the right light receiving system. With this, the light from the projection system can be made incident on the subject's eye from an incidence direction that is even closer to the direction perpendicular to the subject's eye.

In the ophthalmologic microscope system according to the embodiment, the deflection member may be a reflection mirror in which an edge portion of its reflection surface near the pair of objective optical axes is formed in a linear shape, and the edge portion (the edge portion 43a) of the deflection member and the edge portion of the projection system objective lens may be substantially in contact with the optical path of the left light receiving system and the optical path of the right light receiving system.

According to such a configuration, the deflection member and the projection system objective lens can be disposed to be in contact with the optical path of the left light receiving system and the optical path of the right light receiving system. With this, it becomes possible to dispose the deflection member and the projection system objective lens even closer to the objective optical axes of the left light receiving system and the right light receiving system. As a result, the light from the projection system can be made incident on the subject's eye from an incidence direction that is even closer to the direction perpendicular to the subject's eye.

In the ophthalmologic microscope system according to the embodiment, the distance between the lens center of the left objective lens and the lens center of the projection system objective lens, and the distance between the lens center of the right objective lens and the lens center of the projection system objective lens may be substantially equal to each other.

According to such a configuration, it is possible to dispose the optical path of the projection system close to the optical paths of the left light receiving system and the right light receiving system. As a result, the light from the projection system can be made incident on the subject's eye from an incidence direction that is even closer to the direction perpendicular to the subject's eye.

The ophthalmologic microscope system according to the embodiment may include an interference optical system (the OCT system 60) and a data processor (the data processor 200). The interference optical system is configured to split light (the light L0) from an OCT light source (the light source unit 61) into measurement light (the measurement light LS) and reference light (the reference light LR), and detect interference light (the interference light LC) generated from returning light of the measurement light projected by the projection system onto the subject's eye and the reference light. The data processor is configured to generate an image of the subject's eye or an analysis result based on a detection result of the interference light.

In the ophthalmologic microscope system according to the embodiment, the projection system may project treatment light (the treatment light LT) emitted from a treatment laser light source (the treatment light source 81B) and aiming light (the aiming light LA) emitted from an aiming light source (the aiming light source 81A) onto the subject's eye.

In an embodiment, the configuration of the projection system is arbitrary. For example, as described in detail above, the projection system may have at least one of the function of projecting light for OCT (the measurement light LS) onto the subject's eye and the function of projecting light for laser treatment (the aiming light LA and the treatment light LT) onto the subject's eye E. Further, such an embodiment may include a configuration for OCT (such as the OCT system 60 and the data processor 200) and/or a configuration for laser treatment (such as the laser treatment system 80).

In the ophthalmologic microscope system according to the embodiment, the illumination system includes a left illumination system (the left illumination system 10L) and a right illumination system (the right illumination system 10R). The left illumination system is configured to project illumination light onto the subject's eye via the optical path of the left light receiving system. The right illumination system is configured to project illumination light onto the subject's eye via the optical path of the right light receiving system. The left illumination system includes a left optical path coupling member (the beam splitter 11L) configured to coaxially couple the optical path of the left illumination system to the optical path of the left light receiving system. The right illumination system includes a right optical path coupling member (the beam splitter 11R) configured to coaxially couple the optical path of the right illumination system to the optical path of the right light receiving system.

According to such a configuration, it becomes possible to project the light from the projection system onto the subject's eye while performing coaxial illumination on the subject's eye from each of the left light receiving system and the right light receiving system.

MODIFICATION EXAMPLES

The above embodiment is merely an example for implementing the present invention. Those who intend to implement the present invention may apply any modification, omission, addition, substitution, etc. within the scope of the gist of the present invention. Hereinafter, the drawings in the above embodiment will be referred to as needed.

Modification Example 1

In the embodiment described above, the focus lenses 24L and 24R and the wedge prisms 25L and 25R are removed from the optical paths at the time of observing the eye fundus and are inserted into the optical paths at the time of observing the anterior eye segment. Such operations can be automated. In an embodiment, a supplementary optical member for changing the observation site of the subject's eye is employed. For example, the front lens 90 is disposed in the optical paths at the time of observing the eye fundus, and is removed from the optical paths at the time of observing the anterior eye segment.

The ophthalmologic microscope system of the present modification example changes the states of the focus lenses 24L and 24R according to the state of the supplementary optical member (that is, according to the selection of the observation site). In other words, the controller 100 controls a second mechanism for interlockingly operating the focus lenses 24L and 24R according to the change of the observation site by means of the supplementary optical member. Similarly, the controller 100 controls a third mechanism for interlockingly operating the wedge prisms 25L and 25R according to the change of the observation site by means of the supplementary optical member.

A specific example will be described. In response to the removal of the front lens 90 from the optical paths, the controller 100 controls the focusing unit 24A and the optical path deflector 25A to insert the focus lenses 24L and 24R and the wedge prisms 25L and 25R into the respective optical paths. Conversely, in response to the insertion of the front lens 90 into the optical paths, the controller 100 controls the focusing unit 24A and the optical path deflector 25A to remove the focus lenses 24L and 24R and the wedge prisms 25L and 25R from the respective optical paths.

The ophthalmologic microscope system of the present modification example may include a configuration that generates information indicating the state of the supplementary optical member (for example, information indicating whether or not the front lens 90 is inserted into the optical paths). For example, the disposition state of an arm that holds the front lens 90 can be detected by using a sensor such as a micro switch. Alternatively, when a configuration is employed in which the insertion and removal of the front lens 90 is performed based on a signal from the controller 100, the current state of the front lens 90 can be recognized by referring to the history of the control.

As another example, it is possible to determine whether or not the front lens 90 is disposed in the optical paths based on the image(s) acquired by the image sensors 23L and/or 23R and the current states of the focus lenses 24L and 24R and the wedge prisms 25L and 25R. For example, the data processor 200 analyzes an image acquired in the state where the focus lens 24L etc. are disposed in the optical paths to calculate the amount indicating the blur state of this image. When the blur amount is equal to or larger than a threshold value, it is determined that the front lens 90 is disposed in the optical paths. Conversely, when the blur amount is less than the threshold value, it is determined that the front lens 90 is removed from the optical paths. Similar determination of the state of the front lens 90 can also be executed in the case of analyzing an image acquired in the state where the focus lens 24L etc. are removed from the optical paths.

According to the present modification example, the states of the lenses (the focus lenses 24L and 24R) for changing the focal positions and the states of the deflection members (the wedge prisms 25L and 25R) for deflecting the optical paths can be automatically changed in response to the switching of the observation sites. With this, it becomes possible to achieve further improvement in operability.

Modification Example 2

Figure 9:
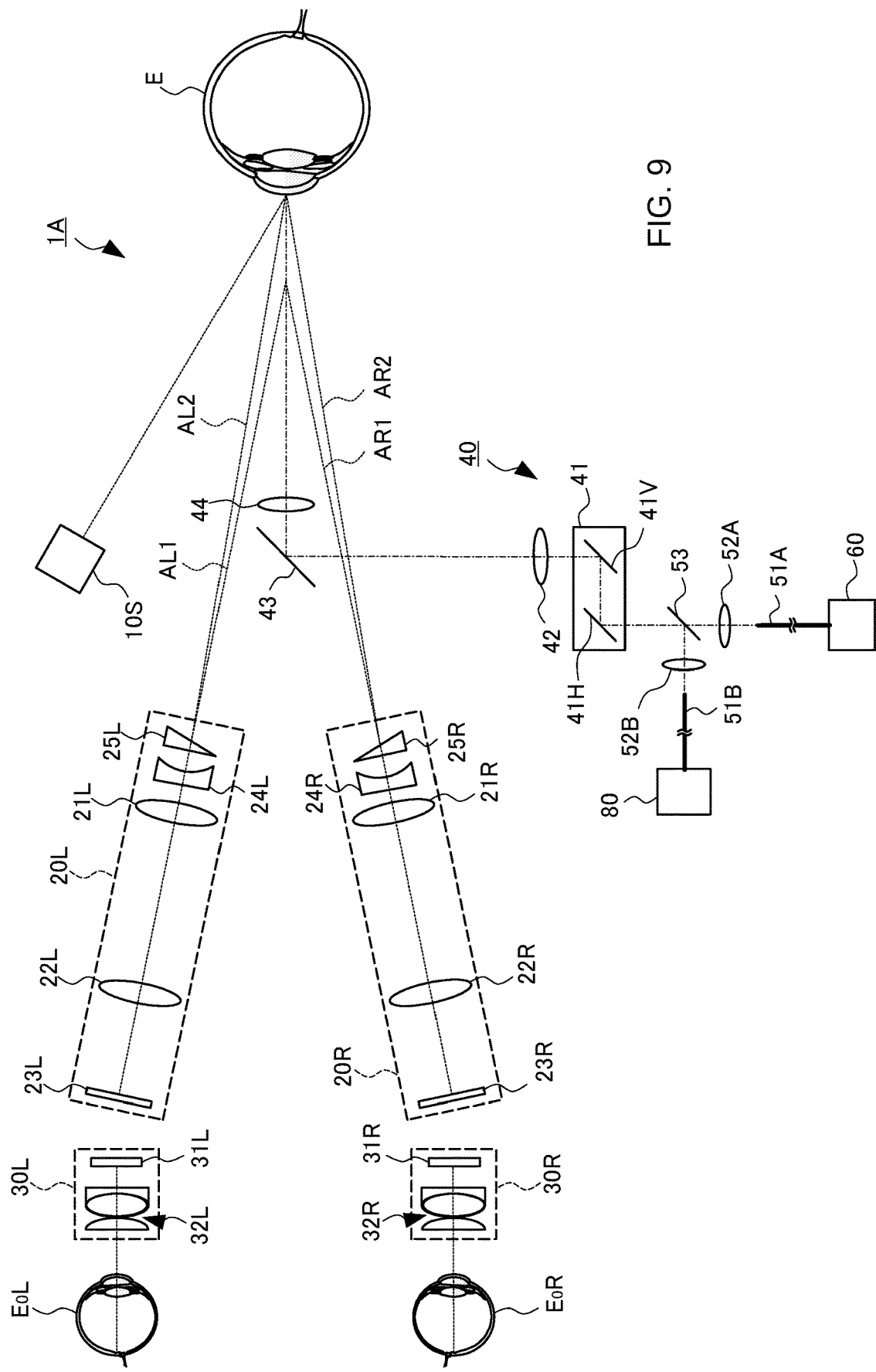
FIG. 9 is a schematic diagram illustrating an example of the configuration of the ophthalmologic microscope system according to the modification example.

The illumination systems (10L and 10R) of the above embodiment are disposed coaxially with the pair of light receiving systems (20L and 20R). The present modification example will describe a configuration in which the illumination systems are disposed non-coaxially with the pair of light receiving systems, that is, a configuration capable of projecting the illumination light from a direction different from those along the objective optical axes of the pair of light receiving systems. An example of the configuration of the optical system according to the present modification example is shown in FIG. 9. The illumination system 10S of the ophthalmologic microscope system 1A can, for example, project slit light onto the subject's eye. A typical example of such an ophthalmologic microscope is a slit lamp microscope. In the present modification example, like the slit lamp microscope, the relative position between the illumination system 10S and the light receiving systems 20L and 20R can be changed. In other words, the illumination system 10S and the light receiving systems 20L and 20R are configured to be rotatable about the same axis. As a result of this, it becomes possible to observe a cross section of the cornea etc. that is being illuminated with the slit light, from an oblique direction.

An ophthalmologic microscope system may include one or both of a coaxial illumination system as in the embodiment described above and a non-coaxial illumination system as in the present modification example. In the case where both illumination systems are included, it is possible to switch the illumination system to be used, for example, in accordance with the switching of the observation sites.

The invention claimed is:

1. An ophthalmologic microscope system comprising:
   an illumination system configured to project illumination light onto a subject's eye;
   a left light receiving system comprising a left objective lens and a left image sensor, and configured to guide returning light of the illumination light that has been projected onto the subject's eye to the left image sensor via the left objective lens;
   a right light receiving system comprising a right objective lens and a right image sensor, and configured to guide returning light of the illumination light that has been projected onto the subject's eye to the right image sensor via the right objective lens, wherein an objective optical axis of the right light receiving system is disposed nonparallelly with respect to an objective optical axis of the left light receiving system;
   a projection system comprising a projection system objective lens, and configured to project light different from the illumination light onto the subject's eye via the projection system objective lens;
   an optical scanner configured for scanning the subject's eye with the light from the projection system; and
   a deflection member disposed in a vicinity of a pair of objective optical axes which are respective optical axes of the left light receiving system and the right light receiving system, disposed in an optical path of the projection system between the optical scanner and the projection system objective lens, and configured to deflect the optical path.

2. The ophthalmologic microscope system of claim 1, wherein
   the optical scanner comprises a one dimensional scanner configured to deflect the light from the projection system in a direction substantially parallel to at least one of the objective axes of the left light receiving system and the right light receiving system, and
   the one dimensional scanner and the deflection member are disposed at positions substantially optically conjugate with each other.

3. The ophthalmologic microscope system of claim 1, wherein
   an edge portion of the projection system objective lens near the pair of objective optical axes is cut out.

4. The ophthalmologic microscope system of claim 3, wherein the deflection member is a reflection mirror wherein an edge portion of a reflection surface near the pair of objective optical axes is formed in a linear shape, and
   the edge portion of the deflection member and the edge portion of the projection system objective lens are substantially in contact with an optical path of the left light receiving system and an optical path of the right light receiving system.

5. The ophthalmologic microscope system of claim 1, wherein
   a distance between a lens center of the left objective lens and a lens center of the projection system objective lens, and a distance between a lens center of the right objective lens and the lens center of the projection system objective lens are substantially equal to each other.

6. The ophthalmologic microscope system of claim 1, further comprising:
   an interference optical system configured to split light from an OCT light source into measurement light and reference light, and detect interference light generated from returning light of the measurement light projected by the projection system onto the subject's eye and the reference light; and
   a data processor configured to generate an image of the subject's eye or an analysis result based on a detection result of the interference light.

7. The ophthalmologic microscope system of claim 1, wherein the projection system projects treatment light emitted from a treatment laser light source and aiming light emitted from an aiming light source onto the subject's eye.

8. The ophthalmologic microscope system of claim 1, wherein the illumination system comprises:
   a left illumination system configured to project illumination light onto the subject's eye via an optical path of the left light receiving system; and
   a right illumination system configured to project illumination light onto the subject's eye via an optical path of the right light receiving system, and wherein
   the left illumination system comprises a left optical path coupling member configured to coaxially couple an optical path of the left illumination system to the optical path of the left light receiving system, and
   the right illumination system comprises a right optical path coupling member configured to coaxially couple an optical path of the right illumination system to the optical path of the right light receiving system.

9. The ophthalmologic microscope system claim 2, wherein a distance between a lens center of the left objective lens and a lens center of the projection system objective lens, and a distance between a lens center of the right objective lens and the lens center of the projection system objective lens are substantially equal to each other.

10. The ophthalmologic microscope system claim 3, wherein a distance between a lens center of the left objective lens and a lens center of the projection system objective lens, and a distance between a lens center of the right objective lens and the lens center of the projection system objective lens are substantially equal to each other.

11. The ophthalmologic microscope system claim 4, wherein a distance between a lens center of the left objective lens and a lens center of the projection system objective lens, and a distance between a lens center of the right objective lens and the lens center of the projection system objective lens are substantially equal to each other.

12. The ophthalmologic microscope system of claim 2, further comprising:
   an interference optical system configured to split light from an OCT light source into measurement light and reference light, and detect interference light generated from returning light of the measurement light projected by the projection system onto the subject's eye and the reference light; and a data processor configured to generate an image of the subject's eye or an analysis result based on a detection result of the interference light.

13. The ophthalmologic microscope system of claim 3, further comprising:
    an interference optical system configured to split light from an OCT light source into measurement light and reference light, and detect interference light generated from returning light of the measurement light projected by the projection system onto the subject's eye and the reference light; and
    a data processor configured to generate an image of the subject's eye or an analysis result based on a detection result of the interference light.

14. The ophthalmologic microscope system of claim 4, further comprising:
    an interference optical system configured to split light from an OCT light source into measurement light and reference light, and detect interference light generated from returning light of the measurement light projected by the projection system onto the subject's eye and the reference light; and
    a data processor configured to generate an image of the subject's eye or an analysis result based on a detection result of the interference light.

15. The ophthalmologic microscope system of claim 2, wherein the projection system projects treatment light emitted from a treatment laser light source and aiming light emitted from an aiming light source onto the subject's eye.

16. The ophthalmologic microscope system of claim 3, wherein the projection system projects treatment light emitted from a treatment laser light source and aiming light emitted from an aiming light source onto the subject's eye.

17. The ophthalmologic microscope system of claim 2, wherein the illumination system comprises:
    a left illumination system configured to project illumination light onto the subject's eye via an optical path of the left light receiving system; and
    a right illumination system configured to project illumination light onto the subject's eye via an optical path of the right light receiving system, and wherein
    the left illumination system comprises a left optical path coupling member configured to coaxially couple an optical path of the left illumination system to the optical path of the left light receiving system, and
    the right illumination system comprises a right optical path coupling member configured to coaxially couple an optical path of the right illumination system to the optical path of the right light receiving system.

18. The ophthalmologic microscope system of claim 3, wherein the illumination system comprises:
    a left illumination system configured to project illumination light onto the subject's eye via an optical path of the left light receiving system; and
    a right illumination system configured to project illumination light onto the subject's eye via an optical path of the right light receiving system, and wherein
    the left illumination system comprises a left optical path coupling member configured to coaxially couple an optical path of the left illumination system to the optical path of the left light receiving system, and
    the right illumination system comprises a right optical path coupling member configured to coaxially couple an optical path of the right illumination system to the optical path of the right light receiving system.

19. The ophthalmologic microscope system of claim 4, wherein the illumination system comprises:
    a left illumination system configured to project illumination light onto the subject's eye via an optical path of the left light receiving system; and
    a right illumination system configured to project illumination light onto the subject's eye via an optical path of the right light receiving system, and wherein
    the left illumination system comprises a left optical path coupling member configured to coaxially couple an optical path of the left illumination system to the optical path of the left light receiving system, and
    the right illumination system comprises a right optical path coupling member configured to coaxially couple an optical path of the right illumination system to the optical path of the right light receiving system.

20. The ophthalmologic microscope system of claim 5, wherein the illumination system comprises:
    a left illumination system configured to project illumination light onto the subject's eye via an optical path of the left light receiving system; and
    a right illumination system configured to project illumination light onto the subject's eye via an optical path of the right light receiving system, and wherein
    the left illumination system comprises a left optical path coupling member configured to coaxially couple an optical path of the left illumination system to the optical path of the left light receiving system, and
    the right illumination system comprises a right optical path coupling member configured to coaxially couple an optical path of the right illumination system to the optical path of the right light receiving system.

* * * * *